US008425403B2

(12) United States Patent
Jo et al.

(10) Patent No.: US 8,425,403 B2
(45) Date of Patent: Apr. 23, 2013

(54) ENDOSCOPE MANIPULATOR FOR MINIMALLY INVASIVE SURGERY

(75) Inventors: Yung-Ho Jo, Gyeonggi-do (KR);
Kwang-Gi Kim, Gyeonggi-do (KR);
Kyoung-Won Nam, Gyeonggi-do (KR);
Young-Woo Kim, Seoul (KR);
Dong-Jun Kim, Gyeonggi-do (KR)

(73) Assignee: National Cancer Center, Gyeonggi-Do (KR)

( * ) Notice: Subject to any disclaimer, the term of this patent is extended or adjusted under 35 U.S.C. 154(b) by 744 days.

(21) Appl. No.: 12/589,444

(22) Filed: Oct. 23, 2009

(65) Prior Publication Data

US 2010/0274079 A1    Oct. 28, 2010

(30) Foreign Application Priority Data

Apr. 28, 2009  (KR) ................. 10-2009-0036851

(51) Int. Cl.
*A61B 1/00*  (2006.01)
(52) U.S. Cl.
USPC ........................ 600/102; 600/103; 600/104
(58) Field of Classification Search ............... 128/897;
600/102–103; 606/1; 901/14–18, 41
See application file for complete search history.

(56) References Cited

U.S. PATENT DOCUMENTS

| | | | | |
|---|---|---|---|---|
| 3,587,872 A | * | 6/1971 | Pauly | 414/732 |
| 4,068,156 A | * | 1/1978 | Johnson et al. | 318/575 |
| 4,273,506 A | * | 6/1981 | Thomson et al. | 414/735 |
| 4,815,006 A | * | 3/1989 | Andersson et al. | 700/254 |
| 4,863,133 A | * | 9/1989 | Bonnell | 248/280.11 |
| 5,159,249 A | * | 10/1992 | Megherbi | 318/568.1 |
| 5,228,429 A | * | 7/1993 | Hatano | 600/102 |

(Continued)

FOREIGN PATENT DOCUMENTS

| | | | |
|---|---|---|---|
| KR | 10-2004-0103212 | * | 12/2004 |
| KR | 1020070023738 A | | 2/2007 |
| KR | 1020090119366 | * | 6/2008 |

OTHER PUBLICATIONS

Mitsuishi, Mamoru et al.; "Development of a Remote Minimally-Invasive Surgical System with Operational Enviroment Transmission Capability"; Proceeding 2003 IEEE on Robotics and Automation; Taipei, Taiwan, Sep. 14-19, 2003.*

(Continued)

*Primary Examiner* — Clayton E Laballe
*Assistant Examiner* — Kevin Butler
(74) *Attorney, Agent, or Firm* — Hamilton, Brook, Smith & Reynolds, P.C.

(57) ABSTRACT

Endoscope manipulator for MIS can overcome disadvantages of multiaxial endoscope manipulator including conventional robot arm and provide compact and lightweight structure to obtain maximum activity space for medical staff. According to the endoscope manipulator for MIS, multi-joint arm is configured so that movement of all of the joints from base link to tip link is manually locked and unlocked by user and not controlled by motors. Additionally, endoscope mounted on an end of multi-joint arm is manipulated using motors to enable movement of three degrees of freedom, thereby accomplishing compact and lightweight endoscope manipulator. Additionally, tube of endoscope can be press-fitted onto tip part of multi-joint arm, and triaxial movement function for vertical, horizontal and forward/backward conveyance of endoscope is implemented in the tip part of multi-joint arm. Therefore, since external manual joints are not moved during operation, Disturbance or restriction to activities of medical staff can be minimized.

14 Claims, 14 Drawing Sheets

U.S. PATENT DOCUMENTS

| | | | | |
|---|---|---|---|---|
| 5,872,892 | A * | 2/1999 | Brown et al. | 700/245 |
| 5,876,325 | A * | 3/1999 | Mizuno et al. | 600/102 |
| 5,907,664 | A * | 5/1999 | Wang et al. | 700/251 |
| 6,432,112 | B2 * | 8/2002 | Brock et al. | 606/130 |
| 6,853,879 | B2 * | 2/2005 | Sunaoshi | 700/253 |
| 2004/0015053 | A1 * | 1/2004 | Bieger et al. | 600/117 |
| 2010/0274078 | A1 | 10/2010 | Kim et al. | |

OTHER PUBLICATIONS

Mayer et al.; The Endo Par System for Minimally Invasive Robotic Surgery; Proceedings of 2004 Intl Conference Intelligent Robots and Systems; Sendal, Japan, Sep. 28-Oct. 2, 2004.*

Oura et al; Development of MRI Compatible Versatile Manipulator for Minimally Invasive Surgery; Waseda University; Tokyo, Japan.*

Guillaume Morel, "Applications of Force Feedback in Medical and Surgical Robotics", Euron Summer School on Medical Robotics, Univerity Pierre et Marie Curie, CNRS, Paris, Frrance, Sep. 2006.*

Peirs et al., A Miniature Manipulator for Integration in a Self-Propelling Endoscope; Elsevier; Dec. 19, 2000.*

Peter-John Christiane, Development of a Minimally Invasive Robotic Surgical Manipulator (submission for masters); Department of Mechanical and Mechatronic Engineering University of Stellenbosch; Dec. 2008.*

Aaron Arthure Kracht; A Linear Base Articulated Robt Arm for Surgical Endoscopy (thesis for Master); North Carolina State University School of Engineering; 2006.*

Neil Munro, Ph.D., D.SC., Robot Manipulator Control Theory and Practice Second Edition, Marcel Dekker, Inc., 2004, Chapter 1 Commercial Robot Manipulators.*

U.S. *non-final* Office Action for U.S. Appl. No. 12/589,439, dated Jul. 31, 2012.

U.S. Notice of Allowance for U.S. Appl. No. 12/589,439, dated Feb. 21, 2013.

* cited by examiner

ENDOSCOPE MANIPULATOR FOR MINIMALLY INVASIVE SURGERY

CROSS-REFERENCE TO RELATED APPLICATION

This application claims priority to and the benefit of Korean Patent Application No. 2009-0036851, filed Apr. 28, 2009, the disclosure of which is incorporated herein by reference in its entirety.

BACKGROUND

1. Technical Field

The present invention relates to an apparatus for manipulating a position of an endoscope used for extending a viewing angle within a human body during minimally invasive surgery and natural orifice transluminal endoscopic surgery, and more particularly, to an endoscope manipulator capable of moving an endoscope in vertical, lateral and longitudinal directions in a compact and lightweight structure.

2. Discussion of Related Art

In general, conventional open surgery for patient treatments causes delay of post-surgical recovery for the patients due to a large incision area and thus a heavy loss of blood, and large scars remaining after the surgery have a negative impact on the patients' lives after the surgery. In order to overcome the above disadvantages of the conventional open surgery, in recent times, novel surgical techniques such as minimally invasive surgery (MIS), natural orifice transluminal endoscopic surgery (NOTES), etc., have been developed.

MIS is a surgical technique of incising and operating on a minimal area of a patient's body using a thin and long surgical instrument specifically configured to minimize an incision area for surgery. NOTES is a surgical technique of inserting a surgical instrument through a natural orifice (for example, the esophagus, the anus, the vagina, etc.) of a human body and conveying the surgical instrument to the operation area in the body to operate on the area without incising the patient's body in order to move the surgical instrument to the operation area in the body. Since MIS and NOTES require only a small incision area for operation and a loss of blood is remarkably less than that of the open surgery, a post-surgical recovery time for the patient is shortened and scarring is minimal. Therefore, in recent times, the number of MIS and NOTES operations has remarkably increased.

When MIS and NOTES are performed, a specifically devised endoscope is used in order to obtain a visual field of an operation area through a minimal incision. That is, the endoscope is a medical imaging device for MIS, in which a visual field of the interior of the patient's body cannot be directly obtained. Surgeons and nurses using MIS perform operations while viewing images of the surgical area obtained through the endoscope.

While performing MIS and NOTES, in order to maximally and accurately show a state of the operation area and movement of the surgical instrument in the patient's body, which are prone to change frequently, positions and visual fields of the endoscope must be continuously varied. In order to manipulate movement of the endoscope throughout the entire operation, movement of the endoscope is currently handled by an assistant surgical operator other than the surgeon, joining the operating team. However, when the exclusive operator who manipulates the endoscope separately joins the operating team, skilled medical operators are unnecessarily used and thus surgical operations are performed less frequently.

In order to solve these problems, in recent times, several endoscope manipulators have been developed to manipulate the endoscope without an exclusive operator. Most of the recently developed endoscope manipulators employ a method of manipulating movement of the endoscope using a robotic technique of a multi-axially controlled robot arm. When the endoscope is manipulated using the robot arm, the position and angle of the endoscope can be accurately adjusted through forward-reverse mechanical analysis of the robot arm. However, since all joints are controlled using motors, loads applied to the joints are increased toward the base joint, thus increasing the total size and weight. In addition, depending on necessity, when the joint of the robot arm is largely moved to adjust a posture of the endoscope, the large movement may disturb or restrict activities of medical staff.

SUMMARY

Example embodiments of the present invention is directed to an endoscope manipulator for MIS capable of overcoming disadvantages of a multiaxial endoscope manipulator including a conventional robot arm and providing a compact and lightweight structure to obtain a maximum activity space for medical staff.

Additional aspects of example embodiments of the invention will be set forth in the description which follows, and in part will be apparent from the description, or may be learned by practice of the invention.

In an example embodiment, an endoscope manipulator for MIS includes: a multi-joint arm; a first plate coupled to an end of the multi-joint arm; a second plate freely rotatably installed over the first plate and to which an endoscope is coupled; and a first driver configured to drive vertical and horizontal rotation of the second plate to vertically and horizontally rotate the endoscope.

In addition, the multi-joint arm may be provided as a multi-joint type manual link that can be locked and unlocked.

Further, the first plate may be coupled to the multi-joint arm by a hinge to be vertically and horizontally rotated, and the hinge may be coupled to a front end rotary shaft of the multi-joint arm to be axially rotated.

Furthermore, the first plate and the second plate may be coupled by a ball joint. Here, a lower part of the ball joint may be freely rotatably coupled to the first plate, and an upper part of the ball joint may be fixed to a lower surface of the second plate.

In addition, the endoscope may be coupled to straightly pass through the first plate, the ball joint and the second plate.

Further, the second plate may have a symmetrical shape with respect to a portion thereof coupled to the ball joint. For example, the second plate may have a Y-shape.

Furthermore, the first driver may selectively drive left and right ends of the second plate to vertically and horizontally rotate the second plate. Here, the first driver may include a pair of drive motors symmetrically fixed to left and right sides of the first plate, and the drive motors may include rotary shafts having male threads engaged with female threads formed at left and right ends of the second plate, respectively.

In addition, the second plate may include gyro-balls installed at the left and right ends, and the gyro-balls may have the female threads.

Further, the endoscope manipulator may further include a second driver configured to convey the endoscope forward and backward. Here, the second driver may include a drive motor fixed to the second plate, and a conveyance block fixed to a conveyance shaft of the drive motor and to which the endoscope is detachably coupled.

Furthermore, the second driver may further include a guide member fixed to an upper part of the second plate to be parallel to the conveyance shaft, and configured to guide conveyance of the conveyance block.

In another example embodiment, an endoscope manipulator for MIS includes: a first plate coupled to an end of a multi-joint arm; a ball joint installed at the first plate; a second plate fixed to the ball joint to be disposed over the first plate and to which an endoscope is coupled; a pair of gyro-balls installed at left and right ends of the second plate; a first driver having a pair of drive motors symmetrically disposed at left and right sides of the first plate, wherein rotary shafts of the drive motors are threadedly engaged with the pair of gyro-balls to vertically and horizontally rotate the second plate for vertical and horizontal rotation of the endoscope; and a second driver installed at the second plate and configured to convey the endoscope forward and backward.

Specific description of other example embodiments will be apparent from the detailed description and the attached drawings.

BRIEF DESCRIPTION OF THE DRAWINGS

The above and other objects, features and advantages of the present invention will become more apparent to those of ordinary skill in the art by describing in detail example embodiments thereof with reference to the attached drawings, in which.

DETAILED DESCRIPTION OF EXAMPLE EMBODIMENTS

Figure 1:
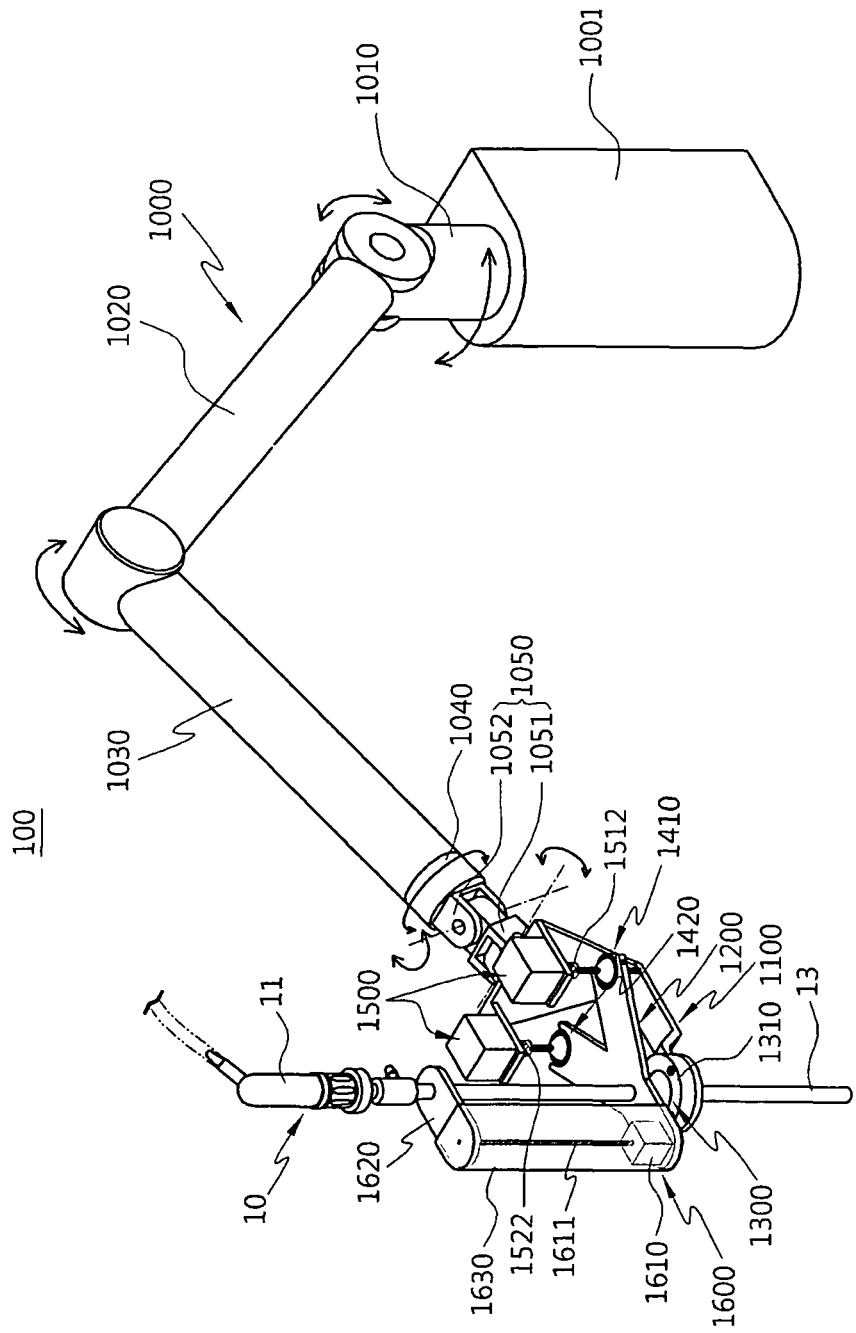
FIG. 1 is a perspective view of an endoscope manipulator for MIS according to an example embodiment of the present invention.

Hereinafter, example embodiments of the present invention will be described in detail. However, the present invention is not limited to the embodiments disclosed below, but can be implemented in various forms. The following embodiments are described in order to enable those of ordinary skill in the art to embody and practice the present invention. Like reference numerals designate like elements throughout the detailed description.

Hereinafter, an endoscope manipulator for MIS in accordance with an example embodiment of the present invention will be described with reference to the accompanying drawings. In the detailed description, if it is determined that description of conventional functions or constitutions may make the sprit of the invention unclear, detailed description thereof will be omitted.

Figure 2:
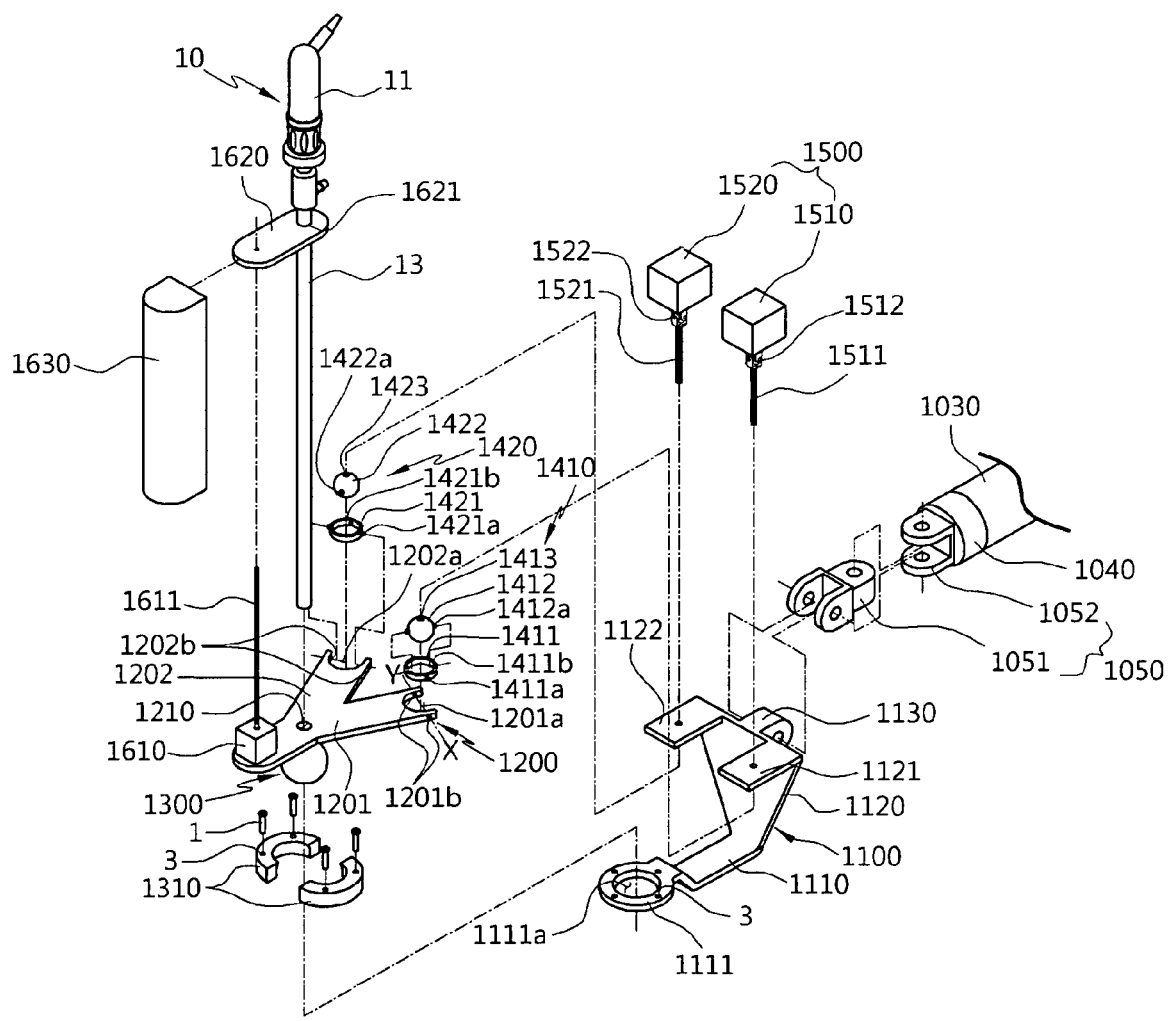
FIG. 2 is an exploded perspective view of the endoscope manipulator for MIS according to an example embodiment of the present invention.
Figure 3:
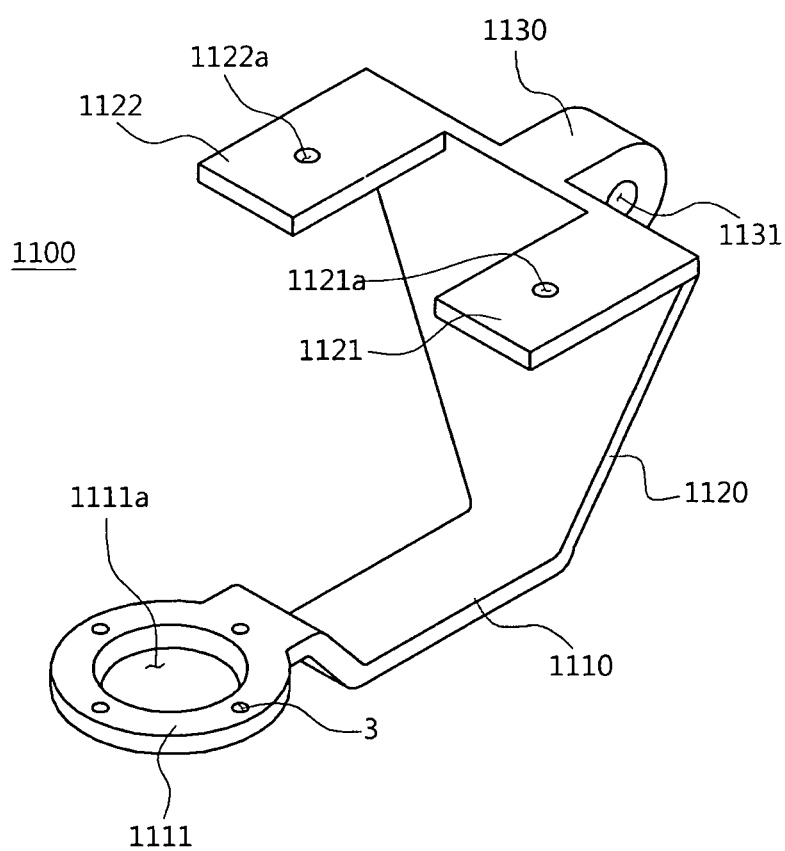
FIG. 3 is a perspective view of a first plate of the endoscope manipulator for MIS according to an example embodiment of the present invention.
Figure 4:
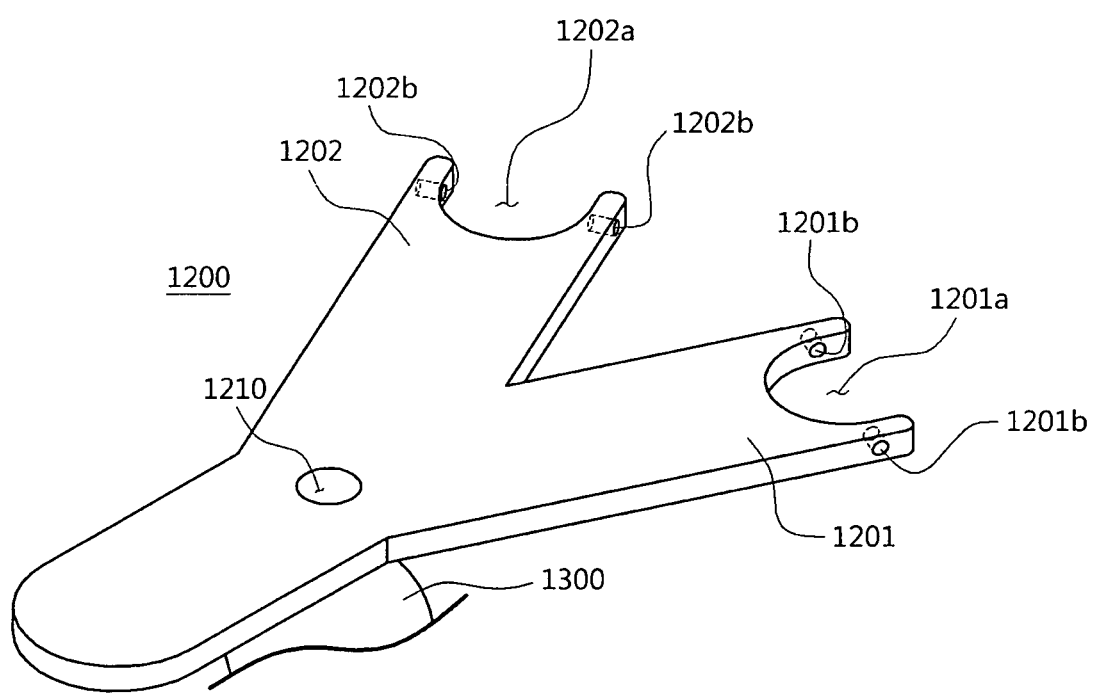
FIG. 4 is a perspective view of a second plate of the endoscope manipulator for MIS according to an example embodiment of the present invention.
Figure 5:
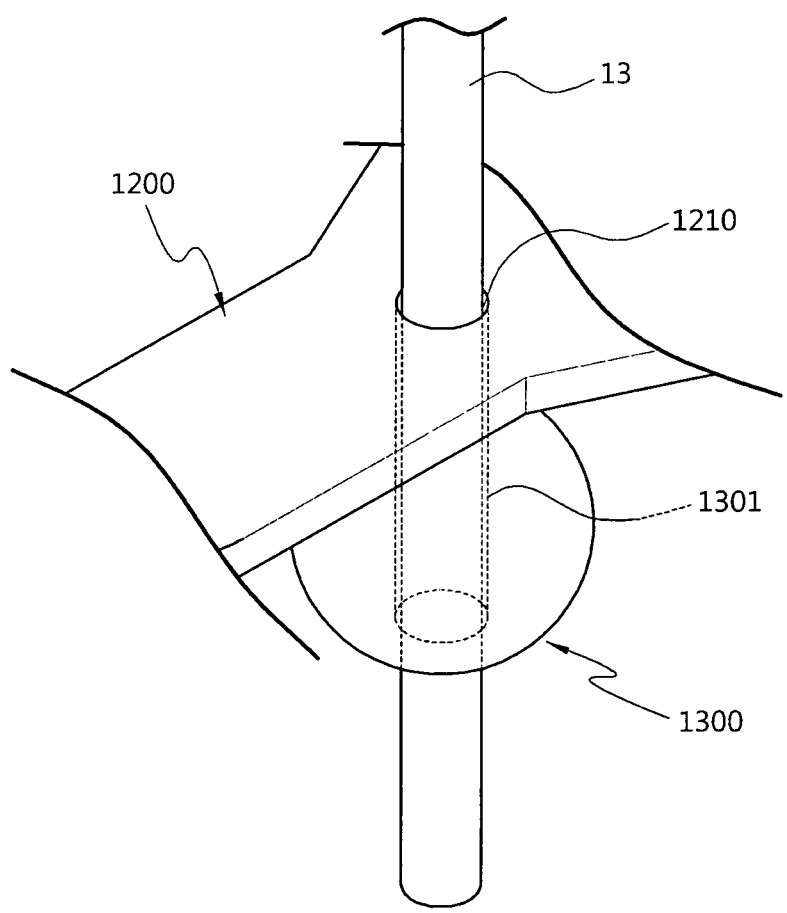
FIG. 5 is a perspective view of a ball joint of the endoscope manipulator for MIS according to an example embodiment of the present invention.
Figure 6:
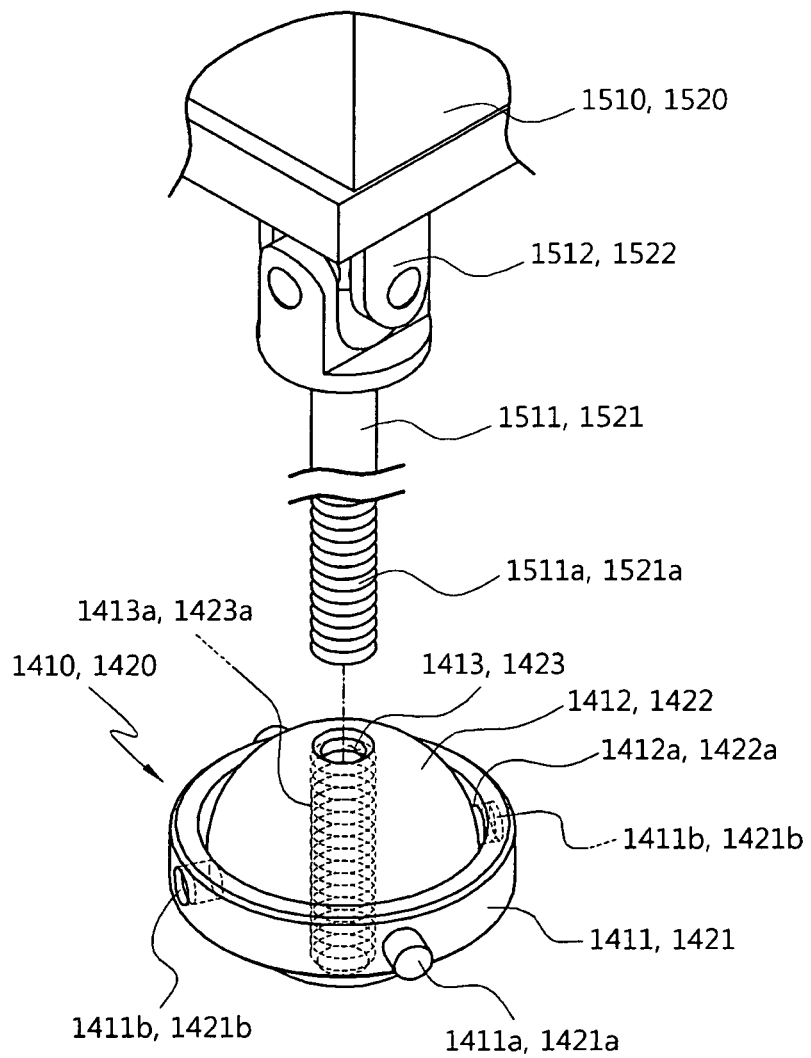
FIG. 6 is a perspective view of a gyroscope of the endoscope manipulator for MIS according to an example embodiment of the present invention.
Figure 7:
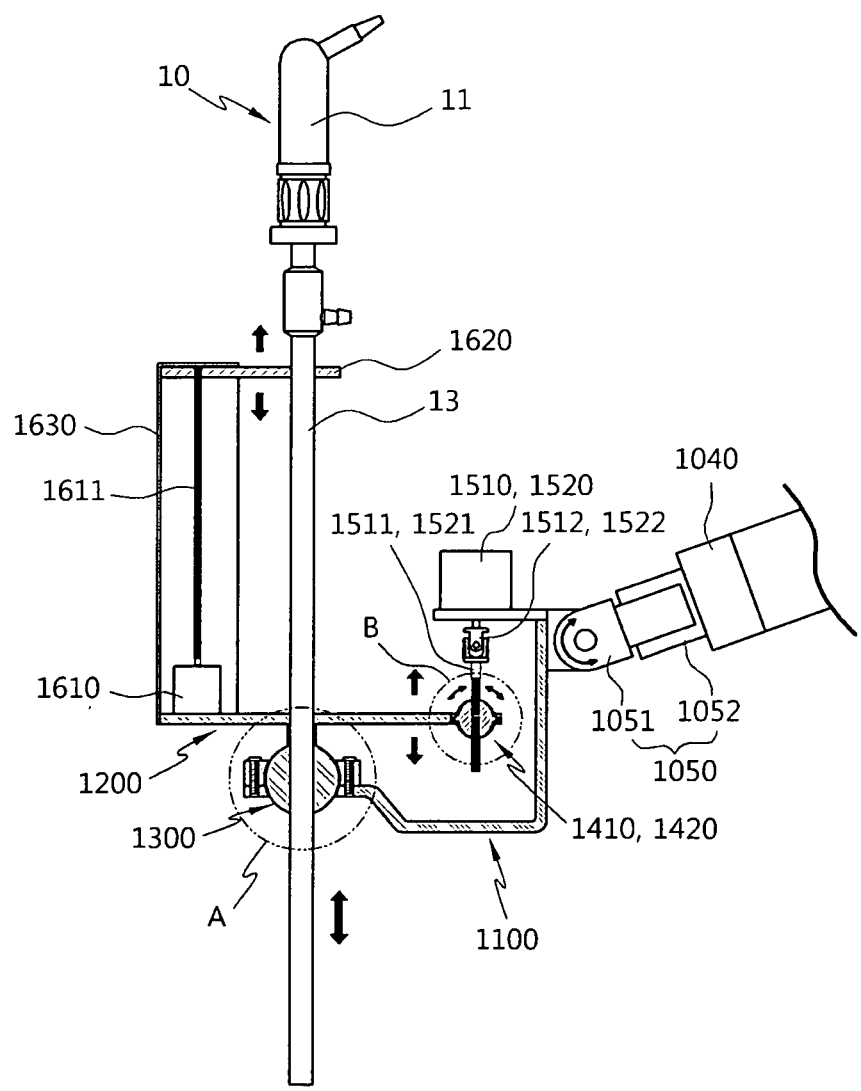
FIG. 7 is a schematic cross-sectional view of the endoscope manipulator for MIS according to an example embodiment of the present invention.
Figure 8:
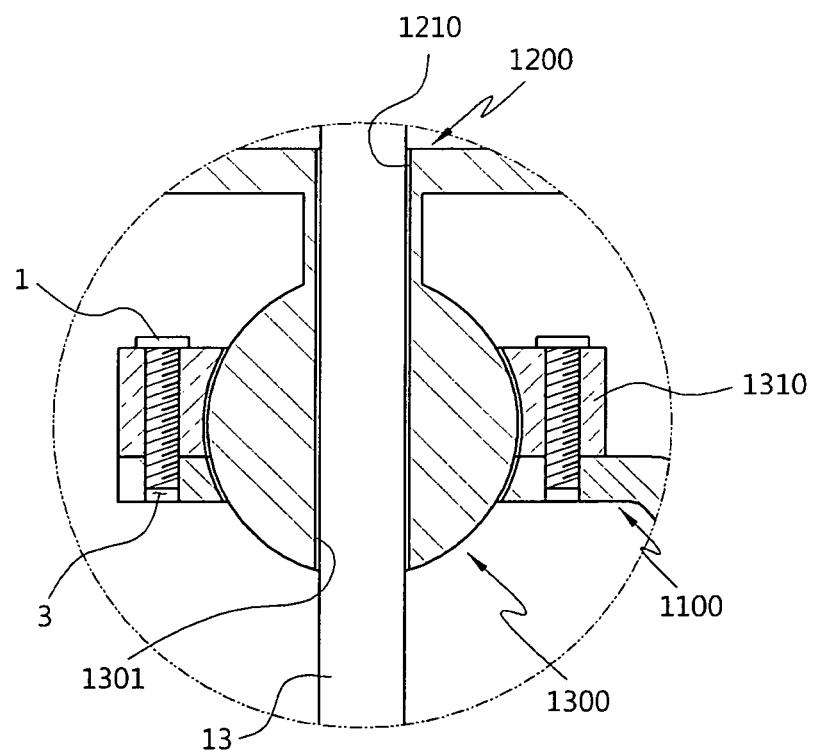
FIG. 8 is an enlarged cross-sectional view of portion A of FIG. 7.
Figure 9:
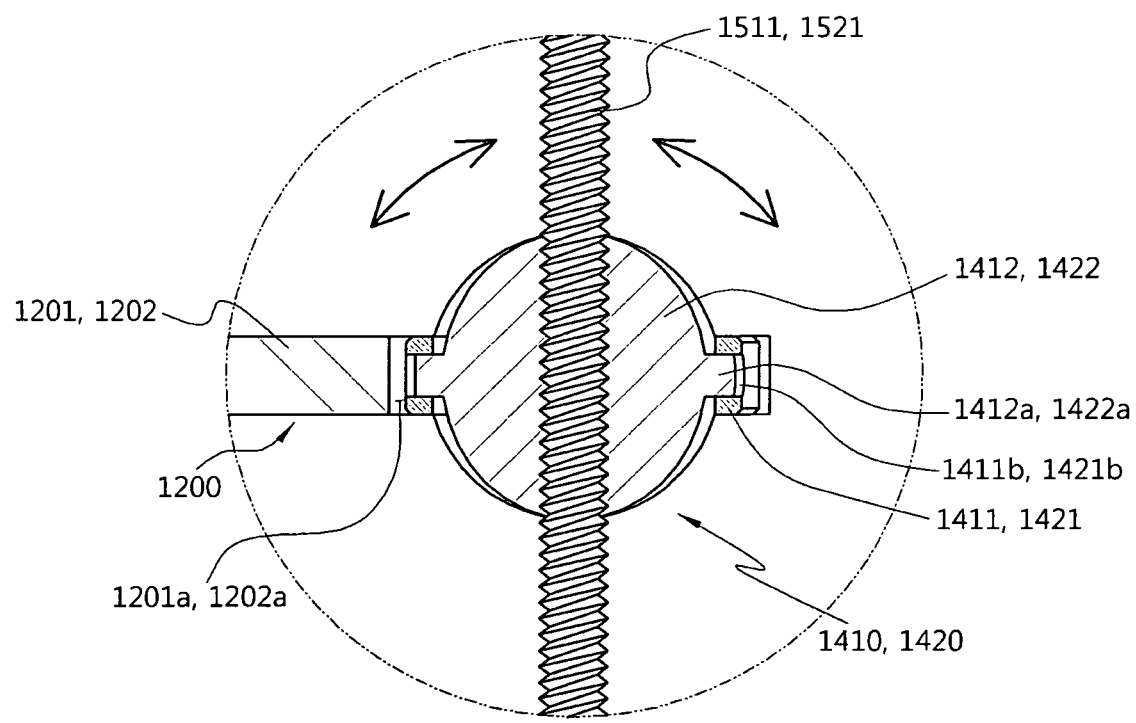
FIG. 9 is an enlarged cross-sectional view of portion B of FIG. 7.

FIGS. 1 and 2 are assembled and exploded perspective views of an endoscope manipulator for MIS according to an example embodiment of the present invention, respectively, FIGS. 3 to 6 are perspective views of a first plate, a second plate, a ball joint and a gyroscope of the endoscope manipulator for MIS according to an example embodiment of the present invention, respectively, FIG. 7 is a schematic cross-sectional view of the endoscope manipulator for MIS according to an example embodiment of the present invention, FIG. 8 is an enlarged cross-sectional view of portion A of FIG. 7, and FIG. 9 is an enlarged cross-sectional view of portion B of FIG. 7.

As shown in FIGS. 1 to 9, an endoscope manipulator 100 for MIS in accordance with an example embodiment of the present invention may include a multi-joint arm 1000, a first plate 1100, a second plate 1200, a ball joint 1300, a pair of gyroscopes 1410 and 1420, a first driver 1500, a second driver 1600, and so on.

The multi-joint arm 1000 may be provided as a multi-joint type manual link connected by at least three links. For example, in this example embodiment, the multi-joint arm 1000 is illustrated as a three joint link constituted by a base link 1010 rotatably coupled to an arm body 1001, an intermediate link 1020 connected to the base link 1010, and a tip link 1030 connected to the intermediate link 1020 and corresponding to an end of the multi-joint arm 1000. However, the multi-joint arm is not limited thereto, and may be provided as various multi-joint structures. Here, the arm body 1001 may be detachably coupled to an operating table (not shown), disposed on a floor near the operating table, or fixed to a ceiling or wall near the operating table. A rotary shaft part 1040 may be installed at a front end of the tip link 1030 so that a hinge 1050 can be axially rotated, which will be described below.

In addition, while not shown, the multi-joint arm 1000 may be configured so that all of the joints can be manually locked and unlocked through a single lever or screw. That is, the multi-joint arm 1000 according to an example embodiment of the present invention may be configured so that movement of all of the joints is manually locked and unlocked by a user, not using a motor. Therefore, by reducing the total weight and size of the multi-joint arm 1000, a compact and lightweight endoscope manipulator 100 is possible, and all of the joints of the multi-joint arm 1000 can be manually locked and unlocked to simply adjust a position thereof.

The first plate 1100 may be coupled to an end of the multi-joint arm 1000 by the hinge 1050 to be vertically and horizontally rotated. Here, the hinge 1050 may include a first hinge 1051 to which a rear end of the first plate 1100 is coupled to be vertically rotated, and a second hinge 1052, to which the first hinge 1051 is coupled to be horizontally rotated. The second hinge 1052 is fixed to the rotary shaft part 1040 at a front end of the multi-joint arm 1000. Here, rotational directions of the first hinge 1051 and the second hinge 1052 are not limited to vertical and horizontal directions, respectively, but may include all constitutions that can be rotated in different rotational directions.

In addition, the first plate 1100 may include a horizontal plate 1110 including a ball joint mounting part 1111 having a circular ball joint hole 1111a formed at a front end thereof, in which a lower part of the ball joint 1300 is inserted to be freely rotated, a vertical plate 1120 having a pair of motor fixing plates 1121 and 1122 bent upwardly from a rear end of the horizontal plate 1110 and to which a pair of drive motors 1510 and 1520 are fixed to both sides thereof, a hinge plate 1130 projecting from a rear end of the vertical plate 1120 to be connected to the hinge 1050, and so on. The ball joint mounting part 1111 has a plurality of screw holes 3 configured to fasten the ball joint using a fixing bracket 1310 with screws 1. Here, an inner diameter of the ball joint hole 1111a is smaller than an outer diameter of the ball joint 1300, the motor fixing plates 1121 and 1122 have shaft holes 1121a and 1122a through which rotary shafts 1511 and 1521 of the drive motors 1510 and 1520 pass, respectively, and the hinge plate 1130 has a pinhole 1131 connected to the hinge 1050.

The second plate 1200 is horizontally disposed over the first plate 1100 to be parallel to the first plate 1100, and coupled by the ball joint 1300 to be freely rotated, for example, vertically and horizontally rotated.

In addition, the second plate 1200 may have a symmetrical shape with respect to a portion thereof coupled to the ball joint 1300. For example, while the example embodiment illustrates the second plate 1200 having a Y shape, the second plate 1200 is not limited thereto, and may have any symmetrical shape.

Further, a pair of gyroscope mounting parts 1201 and 1202 are formed at left and right sides of the second plate 1200 and have semi-circular or circular gyroscope mounting grooves 1201a and 1202a into which a pair of gyroscope bodies 1411 and 1421 having a circular ring-shape are inserted. Here, the pair of gyroscope mounting parts 1201 and 1202 are formed to be symmetrical with respect to the ball joint 1300. The gyroscope mounting parts 1201 and 1202 have first holes 1201b and 1202b through which both first protrusions 1411a and 1421a formed at the gyroscope bodies 1411 and 1421 are inserted to rotate the gyroscope bodies 1411 and 1421 about a first rotary axis X, respectively. Here, the first rotary axis X is consistent with an imaginary straight line connecting the first holes 1201b and 1202b.

In addition, the second plate 1200 has an endoscope hole 1210 through which an endoscope tube 13 passes to mount the endoscope 10. For example, while the example embodiment illustrates a constitution in which the endoscope hole 1210, through which the endoscope tube 13 passes, is formed at a portion coupled to the ball joint 1300 to coincide with the endoscope hole 1301 formed in the ball joint 1300, the constitution is not limited thereto, and an endoscope hole may be formed at a front end of the second plate 1200, not corresponding to the portion coupled to the ball joint 1300. Here, the endoscope 10 is a medical imaging apparatus configured to provide a visual field of an operation area through minimal incision during MIS and NOTES. The conventional endoscope 10 may include a compact charge coupled device (CCD) camera 11, an elongated endoscope tube 13 fastened to the front of the CCD camera 11 and having straightly aligned lenses (not shown) and optical fibers (not shown), an image processor (not shown) and a display part (not shown) configured to output an image obtained through the CCD camera 11, and so on. Since the endoscope 10 is already known in the art, detailed description thereof will be omitted.

The ball joint 1300 is coupled to the first plate 1100 to freely, for example, vertically and horizontally, rotate the second plate 1200. The ball joint 1300 has an entirely spherical shape, and an outer diameter of the ball joint 1300 is larger than an inner diameter of the ball joint hole 1111a.

In addition, the ball joint 1300 has a lower part inserted into the ball joint hole 1111a of the first plate 1100 to be freely rotated, and an upper part projecting in a cylindrical shape to be fixed to a lower surface of the second plate 1200. At this time, the ball joint 1300 is fixed to a substantially center part of the Y-shaped second plate 1200, and the endoscope hole 1301 passing through the center of the spherical ball joint 1300 is formed to coincide with the endoscope hole 1210 in the second plate 1200 such that the endoscope tube 13 can straightly pass through the second plate 1200 and the ball joint 1300.

While the example embodiment illustrates the ball joint 1300 separately manufactured and attached to the lower surface of the second plate 1200, the ball joint 1300 is not limited thereto, and may be integrally formed with the second plate 1200. The lower part of the ball joint 1300 is inserted into the ball joint hole 1111a to be freely rotatably mounted thereon, and then, fastened to the first plate 1100 by at least two semi-circular fixing brackets 1310 with the screws 1.

The gyroscopes 1410 and 1420 may be provided as a pair installed at the gyroscope mounting parts 1201 and 1202 formed at left and right ends of the second plate 1200, and the gyroscopes 1410 and 1420 may include the gyroscope bodies 1411 and 1421, gyro-balls 1412 and 1422, and so on.

The gyroscope bodies 1411 and 1421 have a circular ring shape to be correspondingly inserted into the gyroscope mounting grooves 1201a and 1202a of the gyroscope mounting parts 1201 and 1202. In addition, the gyroscope bodies 1411 and 1421 have the first protrusions 1411a and 1421a formed at both sides thereof to be inserted into the first holes 1201b and 1202b formed in the gyroscope mounting parts 1201 and 1202 to be rotated about the first rotary axis X. Further, the gyroscope bodies 1411 and 1421 have second holes 1411b and 1421b formed at front and rear sides thereof, into which second protrusions 1412a and 1422a of the gyro-balls 1412 and 1422 are inserted to be rotated about a second rotary axis Y. Here, the second rotary axis Y is perpendicular to the first rotary axis X, and coincides with an imaginary straight line connecting the second holes 1411b and 1421b.

The gyro-balls 1412 and 1422 have a substantially spherical shape. An outer diameter of the gyro-balls 1412 and 1422 is smaller than an inner diameter of the ring of the gyroscope bodies 1411 and 1421. The gyro-balls 1412 and 1422 have second protrusions 1412a and 1422a formed at front and rear sides thereof, which are inserted into the second holes 1411b and 1421b formed in the gyroscope bodies 1411 and 1421 to be rotated about the second rotary axis Y.

In addition, the gyro-balls 1412 and 1422 have shaft holes 1413 and 1423 formed therein to correspond to the rotary shafts 1511 and 1521 of the drive motors 1510 and 1520 such that the rotary shafts 1511 and 1521 of the drive motors 1510 and 1520 pass therethrough. Here, the rotary shafts 1511 and 1521 of the drive motors 1510 and 1520 have male threads 1511a and 1521a formed at outer peripheries thereof, and the shaft holes 1413 and 1423 of the gyro-balls 1412 and 1422 have female threads 1413a and 1423a formed at inner peripheries thereof so that the rotary shafts 1511 and 1521 of the drive motors 1510 and 1520 are threadedly engaged with the gyro-balls 1412 and 1422.

The first driver 1500 selectively moves left and right ends of the second plate 1200 to vertically and horizontally rotate the second plate 1200.

The first driver 1500 may include the pair of drive motors 1510 and 1520 fixed to the pair of motor fixing plates 1121 and 1122 symmetrically provided at both sides of the vertical plate 1120 of the first plate 1100. The rotary shafts 1511 and 1521 of the drive motors 1510 and 1520 are disposed substantially perpendicular to the second plate 1200, and inserted to pass through the shaft holes 1121a and 1122a of the motor fixing plates 1121 and 1122 and the shaft holes 1413 and 1423 of the gyro-balls 1412 and 1422. The rotary shafts 1511 and 1521 of the drive motors 1510 and 1520 have the male threads 1511a and 1521a formed at outer peripheries thereof to be threadedly engaged with the female threads 1413a and 1423a formed at inner peripheries of the shaft holes 1413 and 1423 of the gyro-balls 1412 and 1422, respectively. In addition, universal joints 1512 and 1522 may be installed between the drive motors 1510 and 1520 and the rotary shafts 1511 and 1521 thereof so that two-dimensional rotation of the gyroscopes 1410 and 1420 can be performed in a state in which the rotary shafts 1511 and 1521 of the drive motors 1510 and 1520 and the shaft holes 1413 and 1423 of the gyro-balls 1412 and 1422 continuously maintain a straight line. That is, they are connected in a sequence of the drive motors 1510 and 1520—universal joints 1512 and 1522—rotary shafts 1511 and 1521—gyroscopes 1410 and 1420. While the example embodiment shows a constitution in which the drive motors 1510 and 1520 are fixed to the motor fixing plates 1121 and 1122, and the universal joints 1512 and 1522 are installed between the drive motors 1510 and 1520 and the rotary shafts 1511 and 1521 to two-dimensionally rotate the gyroscopes 1410 and 1420, the constitution is not limited thereto, and may be provided in various constitutions. For example, the drive motors 1510 and 1520 may be installed at the motor fixing plates 1121 and 1122 to move within a predetermined interval in X- and Y-axis directions (see FIG. 2) to enable two-dimensional rotation of the gyroscopes 1410 and 1420, without using the universal joints 1512 and 1522 of the example embodiment.

The second driver 1600 is installed at the second plate 1200 to move the endoscope tube 13 forward and backward.

The second driver 1600 may include a drive motor 1610, a conveyance block 1620, a guide member 1630, and so on.

The drive motor 1610 is fixed to an upper surface of a front end of the second plate 1200. Here, since the drive motor 1610 is a linear motor, which is already known in the art, detailed descriptions thereof will be omitted.

The conveyance block 1620 is fixed to an end of a conveyance shaft 1611 of the drive motor 1610 and has an endoscope coupling hole 1621 through which the endoscope tube 13 is detachably inserted to move the endoscope tube 13 forward and backward.

The guide member 1630 has a rectangular parallelepiped or cylindrical shape, at least one surface of which is opened, and a lower end of the guide member 1630 is fixed to an upper surface of the second plate 1200 to be parallel to the conveyance shaft 1611 of the drive motor 1610 to move the conveyance block 1620 forward and backward.

The endoscope manipulator 100 for MIS in accordance with an example embodiment of the present invention may continuously adjust the position and viewing direction of the endoscope in order to maximally widely and accurately show the state of the operating area and movement of the surgical instrument in the patient's body, which are prone to change frequently during performance of MIS and NOTES. In order to adjust movement of the endoscope 10 throughout the operation, first, after fixing the arm body 1001 of the multi-joint arm 1000 to the operation table, all of the joints from the base link 1010 to the tip link 1030 are manually manipulated such that the endoscope tube 13 fitted onto the tip part of the multi-joint arm 1000 can be inserted into an incision area of the patient. After adjusting positions of all of the joints of the multi-joint arm 1000, the multi-joint arm 1000 is securely fixed by locking the joints using a single lever or screw. Next, the endoscope 10 mounted on the tip part of the multi-joint arm 1000 is adjusted by motors 1410, 1510 and 1610 to enable three degrees of freedom of movement, showing the state of the operating area and movement of the surgical instrument in the patient's body, which are prone to change frequently, through minimal incision.

Hereinafter, operations of the endoscope manipulator for MIS in accordance with an example embodiment of the present invention will be described with reference to FIGS. 10 to 14.

Figure 10:
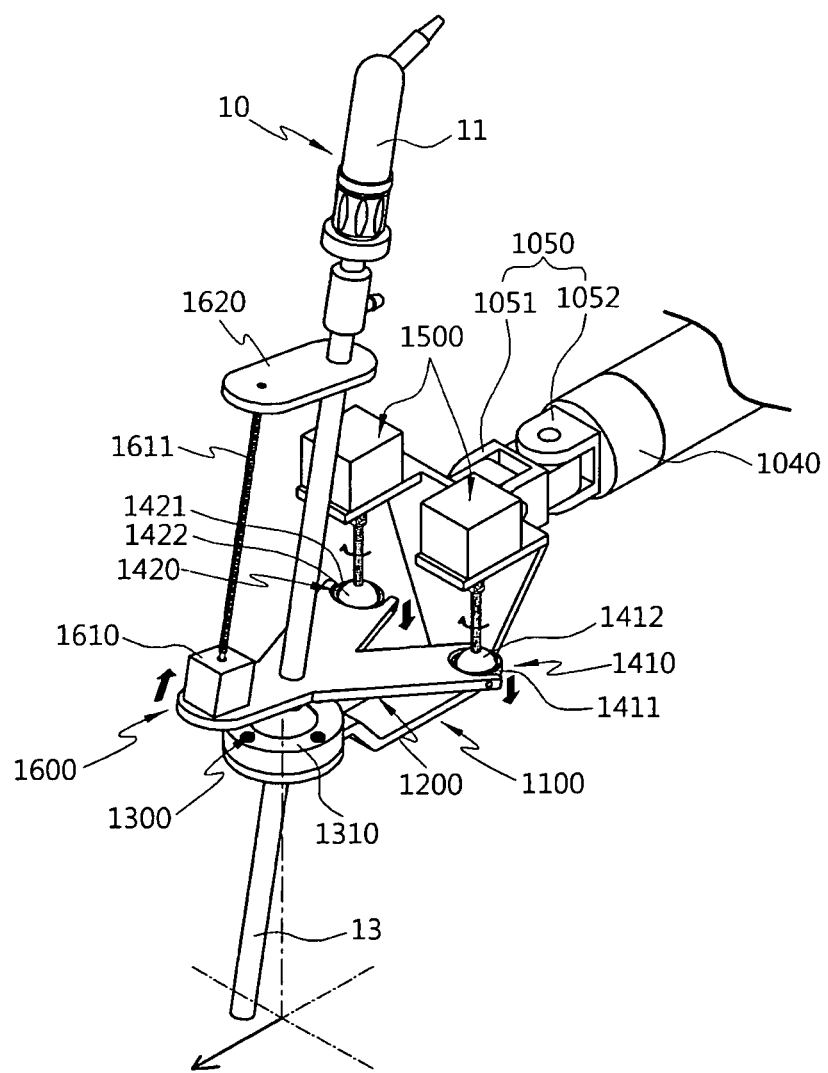
FIGS. 10 and 11 show vertical rotation of the endoscope using the endoscope manipulator for MIS according to an example embodiment of the present invention.
Figure 11:
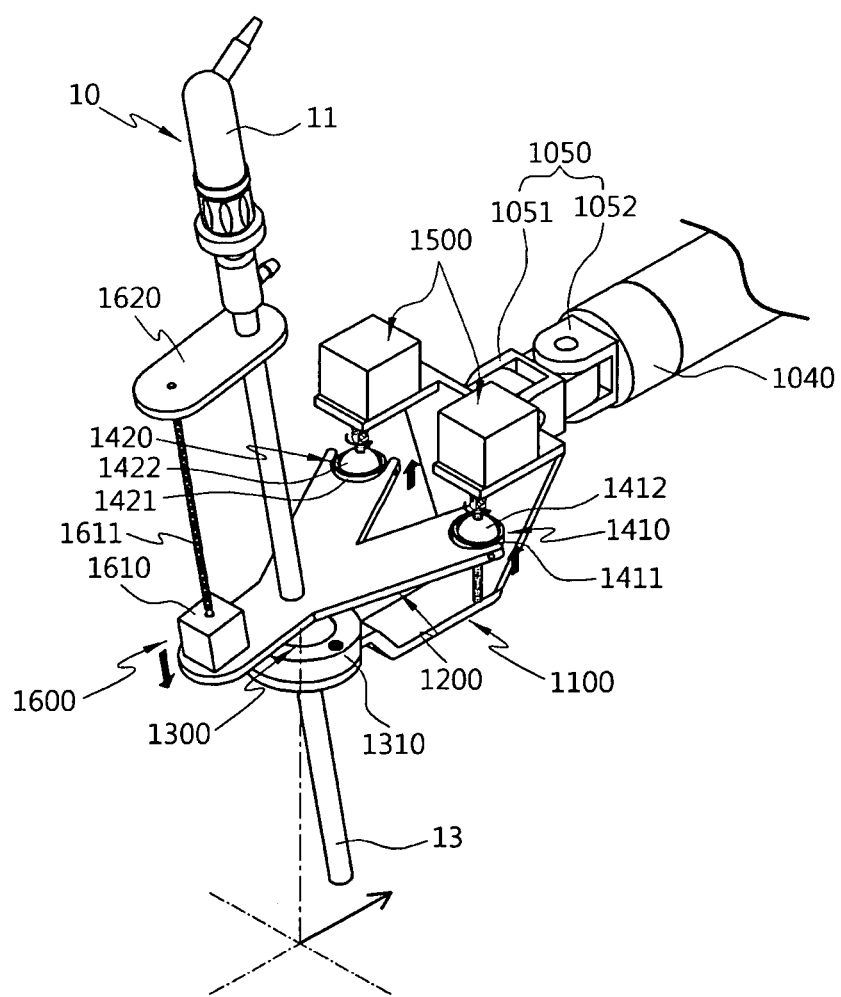

FIGS. 10 and 11 show vertical rotation of the endoscope using the endoscope manipulator for MIS according to an example embodiment of the present invention.

First, as shown in FIG. 10, when the pair of drive motors 1510 and 1520 fixed to the first plate 1100 are rotated in the same direction, for example, clockwise, left and right ends of a rear end of the second plate 1200 are lowered by the gyro-balls 1412 and 1422 threadedly engaged with the rotary shafts 1511 and 1521 of the drive motors 1510 and 1520, respectively. Here, the universal joints 1512 and 1522 are installed between the drive motors 1510 and 1520 and the rotary shafts 1511 and 1521 thereof, and the gyro-balls 1412 and 1422 are gyro-movably mounted on the gyroscope mounting parts 1201 and 1202 of the second plate 1200. As a result, even when the rotary shafts 1511 and 1521 of the drive motors 1510 and 1520 are rotated to lower the left and right ends of the rear end of the second plate 1200, the rotary shafts 1511 and 1521 of the drive motors 1510 and 1520 and the shaft holes 1413 and 1423 of the gyro-balls 1412 and 1422 continuously maintain a straight line. Therefore, since the second plate 1200 is freely rotatably coupled to an upper part of the first plate 1100 by the ball joint 1300, the rear end of the second plate 1200 is lowered to upwardly rotate an end of the endoscope tube 13 about the ball joint 1300.

Next, as shown in FIG. 11, when the pair of drive motors 1510 and 1520 fixed to the first plate 1100 are rotated counterclockwise, the left and right ends of the rear end of the second plate 1200 are raised by the gyro-balls 1412 and 1422 threadedly engaged with the rotary shafts 1511 and 1521 of the drive motors 1510 and 1520, respectively. Here, the universal joints 1512 and 1522 are installed between the drive motors 1510 and 1520 and the rotary shafts 1511 and 1521 thereof, and the gyro-balls 1412 and 1422 are gyro-movably mounted on the gyroscope mounting parts 1201 and 1202 of the second plate 1200. As a result, even when the rotary shafts 1511 and 1521 of the drive motors 1510 and 1520 are rotated to raise the left and right ends of the rear end of the second plate 1200, the rotary shafts 1511 and 1521 of the drive motors 1510 and 1520 and the shaft holes 1413 and 1423 of the gyro-balls 1412 and 1422 continuously maintain a straight line. Therefore, since the second plate 1200 is freely rotatably coupled to the upper part of the first plate 1100 by the ball joint 1300, the rear end of the second plate 1200 is raised to downwardly rotate the end of the endoscope tube 13 about the ball joint 1300.

Figure 12:
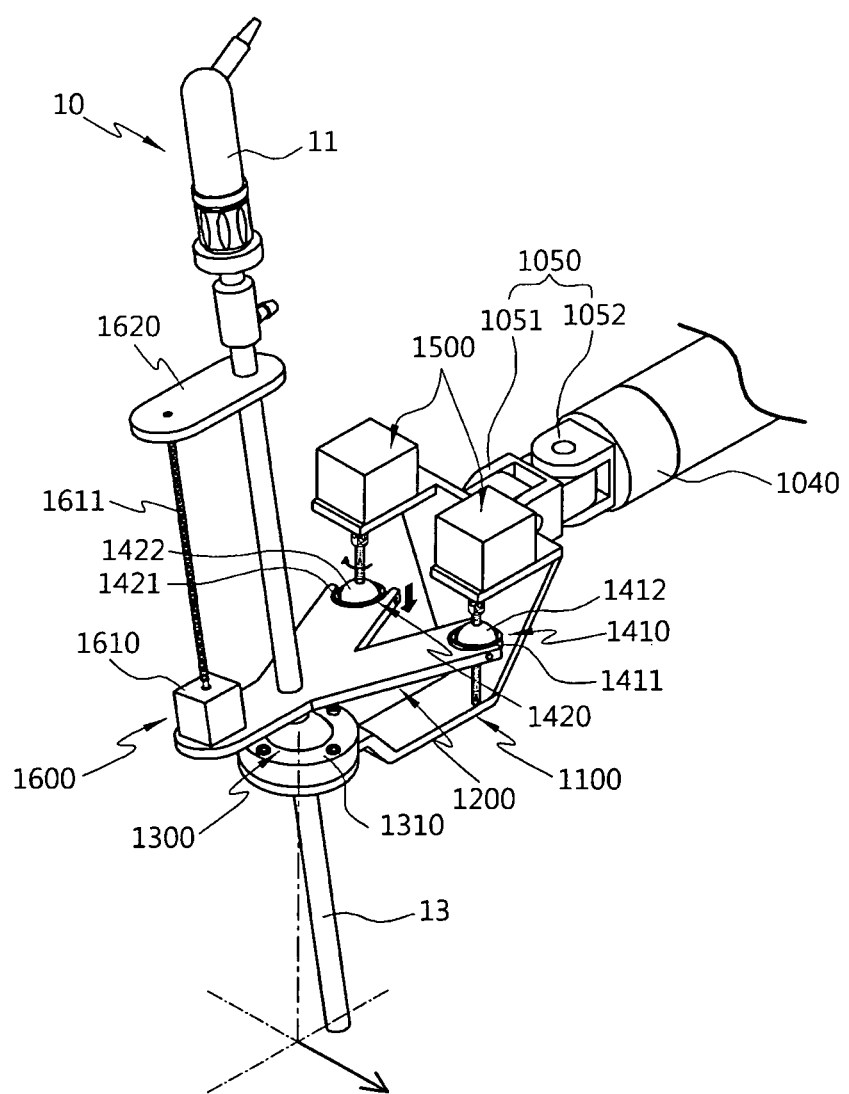
FIGS. 12 and 13 show horizontal rotation of the endoscope using the endoscope manipulator for MIS according to an example embodiment of the present invention.
Figure 13:
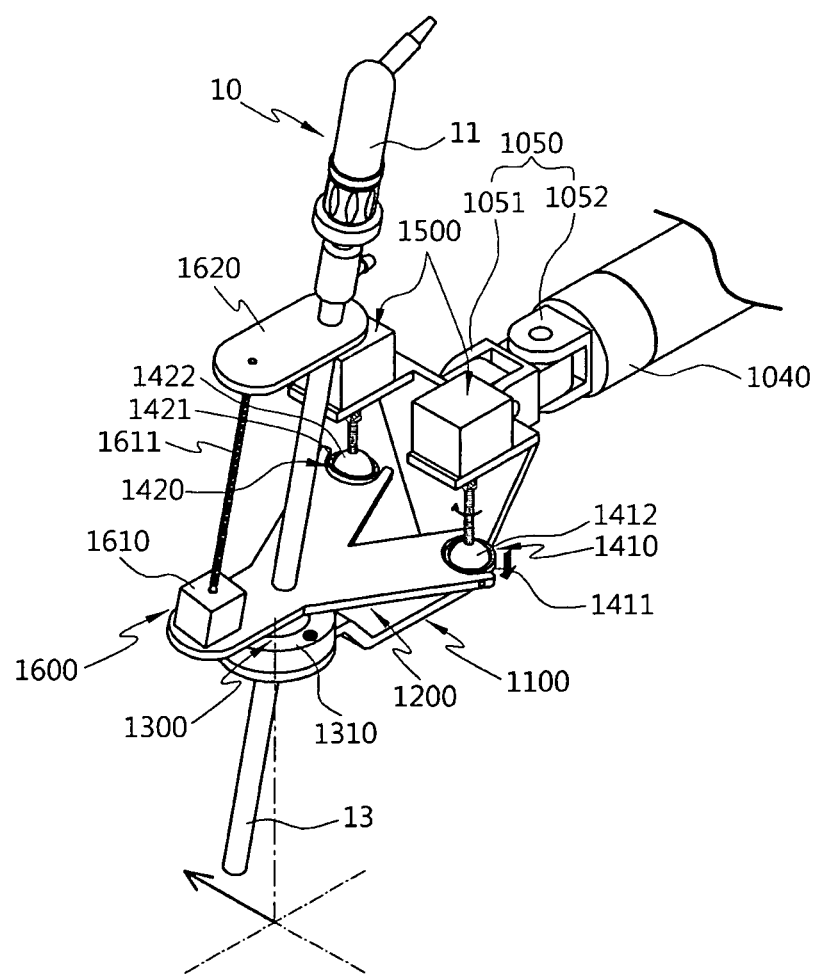

FIGS. 12 and 13 show horizontal rotation of the endoscope using the endoscope manipulator for MIS according to an example embodiment of the present invention.

First, as shown in FIG. 12, when the right drive motor 1520 of the pair of drive motors 1510 and 1520 fixed to the first plate 1100 is rotated clockwise, the right end of the rear end of the second plate 1200 is lowered more than the left end by the right gyro-ball 1422 threadedly engaged with the rotary shaft 1521 of the right drive motor 1520. Here, the universal joints 1512 and 1522 are installed between the drive motors 1510 and 1520 and the rotary shafts 1511 and 1521 thereof, and the gyro-balls 1412 and 1422 are gyro-movably mounted on the gyroscope mounting parts 1201 and 1202 of the second plate 1200. As a result, even when the rotary shaft 1521 of the right drive motor 1520 is rotated to lower the right end of the rear end of the second plate 1200, the rotary shafts 1511 and 1521 of the drive motors 1510 and 1520 and the shaft holes 1413 and 1423 of the gyro-balls 1412 and 1422 continuously maintain a straight line. Therefore, since the second plate 1200 is freely rotatably coupled to the upper part of the first plate 1100 by the ball joint 1300, the second plate 1200 is inclined rightward and then the end of the endoscope tube 13 is rotated leftward about the ball joint 1300.

Next, as shown in FIG. 13, when the left drive motor 1510 of the pair of drive motors 1510 and 1520 fixed to the first plate 1100 is rotated clockwise, the left end of the rear end of the second plate 1200 is lowered more than the right end by the left gyro-ball 1412 threadedly engaged with the rotary shaft 1511 of the left drive motor 1510. Here, the universal joints 1512 and 1522 are installed between the drive motors 1510 and 1520 and the rotary shafts 1511 and 1521 thereof, and the gyro-balls 1412 and 1422 are gyro-movably mounted on the gyroscope mounting parts 1201 and 1202 of the second plate 1200. As a result, even when the rotary shaft 1511 of the left drive motor 1510 is rotated to lower the left end of the rear end of the second plate 1200, the rotary shafts 1511 and 1521 of the drive motors 1510 and 1520 and the shaft holes 1413 and 1423 of the gyro-balls 1412 and 1422 continuously maintain a straight line. Therefore, since the second plate 1200 is freely rotatably coupled to the upper part of the first plate 1100 by the ball joint 1300, the second plate 1200 is inclined leftward to rotate the end of the endoscope tube 13 rightward about the ball joint 1300.

While the example embodiment illustrates that any one of the pair of drive motors 1510 and 1520 is rotated to horizontally rotate the endoscope tube 13, the example embodiment is not limited thereto, and may include a constitution in which the pair of drive motors 1510 and 1520 are simultaneously rotated in opposite directions to horizontally rotate the endoscope tube 13.

Figure 14:
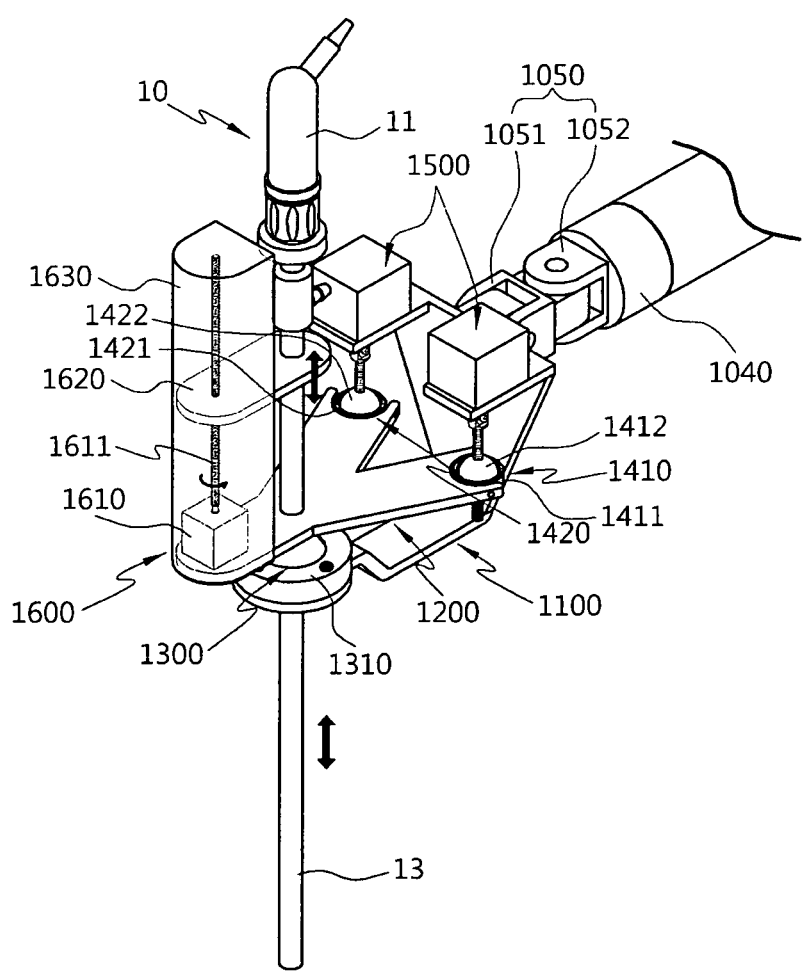
FIG. 14 shows forward/backward conveyance of the endoscope using the endoscope manipulator for MIS according to an example embodiment of the present invention.

FIG. 14 shows forward/backward conveyance of the endoscope using the endoscope manipulator for MIS according to an example embodiment of the present invention.

As shown in FIG. 14, when the drive motor 1610 is driven in a state in which the endoscope tube 13 is detachably inserted into the endoscope coupling hole 1621 of the conveyance block 1620, the conveyance block 1620 moves along the guide member 1630 forward and backward. Here, the endoscope tube 13 moves with the conveyance block 1620 to pass through and move the endoscope hole 1301 of the first ball joint 1300 and the second plate 1200 forward and backward.

In addition, while not shown, a surgeon may directly manipulate the triaxial movement for vertical, horizontal and forward/backward conveyance of the endoscope tube 13 using a foot pedal or joystick connected to a controller configured to control the respective motors 1510, 1520 and 1610 of the first driver 1500 and the second driver 1600. In addition, a motor (not shown) may be further installed at the conveyance block 1620 to rotate the endoscope tube 13 itself.

As described above, according to the endoscope manipulator 100 for MIS in accordance with an example embodiment of the present invention, the multi-joint arm 1000 is configured so that movement of all of the joints from the base link 1010 to the tip link 1030 is manually locked and unlocked by a user and not controlled by motors. In addition, the endoscope 10 mounted on an end of the multi-joint arm 1000 is manipulated using the motors 1410, 1510 and 1610 to enable movement of three degrees of freedom, thereby accomplishing a compact and lightweight endoscope manipulator 100. In addition, the endoscope tube 13 can be press-fitted onto the tip part of the multi-joint arm 1000, and a triaxial movement function for vertical, horizontal and forward/backward conveyance of the endoscope tube 13 is implemented in the tip part of the multi-joint arm 1000. As a result, since external manual joints are not moved during the operation, it is possible to minimize disturbance or restriction to activities of medical staff.

In an endoscope manipulator for MIS in accordance with an example embodiment of the present invention, a multi-joint arm is configured so that movement of all of the joints from a base link to a tip link is manually locked-unlocked by a user and not controlled by motors. In addition, the endoscope mounted on an end of the multi-joint arm is manipulated using motors to enable movement of three degrees of freedom, thereby accomplishing a compact and light weight endoscope manipulator.

In addition, a tube of the endoscope can be press-fitted onto a tip part of the multi-joint arm, and a triaxial movement function for vertical, lateral and forward/backward conveyance of the endoscope is implemented in the tip part of the multi-joint arm. As a result, since external manual joints are not moved during the operation, it is possible to minimize disturbance or restriction to activities of medical staff.

Further, only a fastening part of the tip part of the multi-joint arm constituted by the external manual joints is partially modified to modularize the triaxial control tip and the multi-joint arm so that it can have various lengths and shapes depending on the kinds of operations.

Furthermore, a triaxial control tip appropriate to the kinds of the endoscope used in medical institutions is provided and various triaxial control tips can be exchanged to a single multi-joint arm so that a single standardized multi-joint arm and several individual triaxial control tips are provided as a set to allow doctors to use various endoscopes according to personal preferences.

While the invention has been shown and described with reference to certain example embodiments thereof, it will be understood by those skilled in the art that various changes in form and details may be made therein without departing from the spirit and scope of the invention as defined by the appended claims.

What is claimed is:

1. An endoscope manipulator for minimally invasive surgery, comprising:
 a multi joint arm;
 a first plate coupled to an end of the multi joint arm;
 a second plate freely rotatably installed over the first plate and to which an endoscope is coupled; and
 a first driver configured to drive vertical and horizontal rotation of the second plate to substantially vertically and horizontally rotate the endoscope; and
 a second driver configured to convey the endoscope forward and backward
 wherein the second driver comprises;
 a drive motor fixed to the second plate; and
 a conveyance block fixed to a conveyance shaft of the drive motor and to which the endoscope is detachably coupled.

2. The endoscope manipulator according to claim 1, wherein the multi joint arm is provided as a multi joint type manual link.

3. The endoscope manipulator according to claim 1, wherein the first plate is coupled to the multi joint arm by a hinge to be substantially vertically and horizontally rotated.

4. The endoscope manipulator according to claim 3, wherein the hinge is coupled to a front end rotary shaft of the multi joint arm to be axially rotated.

5. The endoscope manipulator according to claim 1, wherein the first plate and the second plate are coupled by a ball joint.

6. The endoscope manipulator according to claim 5, wherein a lower part of the ball joint is freely rotatably coupled to the first plate, and an upper part of the ball joint is fixed to a lower surface of the second plate.

7. The endoscope manipulator according to claim 5, wherein the endoscope is coupled to straightly pass through the first plate, the ball joint and the second plate.

8. The endoscope manipulator according to claim 5, wherein the second plate has a symmetrical shape with respect to a portion thereof coupled to the ball joint.

9. The endoscope manipulator according to claim 8, wherein the second plate has a Y-shape.

10. The endoscope manipulator according to claim 8, wherein the first driver selectively drives left and right ends of the second plate to substantially vertically and horizontally rotate the second plate.

11. The endoscope manipulator according to claim 10, wherein the first driver comprises a pair of drive motors symmetrically fixed to left and right sides of the first plate, and the drive motors have rotary shafts having male threads engaged with female threads formed at the left and right ends of the second plate, respectively.

12. The endoscope manipulator according to claim 11, wherein the second plate comprises gyro-balls installed at the left and right ends, and the gyro-balls have the female threads.

13. The endoscope manipulator according to claim 1, wherein the second driver further comprises a guide member fixed to an upper part of the second plate to be parallel to the conveyance shaft, and configured to guide conveyance of the conveyance block.

14. An endoscope manipulator for minimally invasive surgery, comprising:
 a first plate coupled to an end of a multi joint arm;
 a ball joint installed at the first plate;
 a second plate fixed to the ball joint to be disposed over the first plate and to which an endoscope is coupled;
 a pair of gyro-balls installed at left and right ends of the second plate;
 a first driver having a pair of drive motors symmetrically disposed at left and right sides of the first plate, wherein rotary shafts of the drive motors are threadedly engaged with the pair of gyro-balls to substantially vertically and horizontally rotate the second plate for vertical and horizontal rotation of the endoscope; and
 a second driver installed at the second plate and configured to convey the endoscope forward and backward.

* * * * *